United States Patent
Mukkamala et al.

(10) Patent No.: US 10,349,838 B2
(45) Date of Patent: Jul. 16, 2019

(54) METHODS AND APPARATUS FOR DETERMINING ARTERIAL PULSE WAVE VELOCITY

(75) Inventors: Ramakrishna Mukkamala, Okemos, MI (US); Da Xu, Burnaby (CA); Guanqun Zhang, East Lansing, MI (US); Mingwu Gao, East Lansing, MI (US); Mohsen Moslehpour, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1826 days.

(21) Appl. No.: 13/816,427

(22) PCT Filed: Aug. 12, 2011

(86) PCT No.: PCT/US2011/047516
§ 371 (c)(1),
(2), (4) Date: Mar. 29, 2013

(87) PCT Pub. No.: WO2012/021765
PCT Pub. Date: Feb. 16, 2012

(65) Prior Publication Data
US 2013/0184595 A1    Jul. 18, 2013

Related U.S. Application Data

(60) Provisional application No. 61/372,958, filed on Aug. 12, 2010.

(51) Int. Cl.
*A61B 5/021* (2006.01)
*A61B 5/0285* (2006.01)
(Continued)

(52) U.S. Cl.
CPC .......... *A61B 5/02125* (2013.01); *A61B 5/029* (2013.01); *A61B 5/0285* (2013.01); *A61B 5/7235* (2013.01); *A61B 5/7278* (2013.01)

(58) Field of Classification Search
None
See application file for complete search history.

(56) References Cited

U.S. PATENT DOCUMENTS 5,241,964 A * 9/1993 McQuilkin ........ A61B 5/02125
600/485
5,437,285 A  8/1995 Verrier et al.
(Continued)

OTHER PUBLICATIONS

Maguire et al, "A Comparative Study in the Use of Brachial Photoplethysmography and the QRS Complex as Timing References in Determination of Pulse Transit Time", 2001, 'Engineering in Medicine and Biology Society, 2001, Proceedings of the 23rd Annual international Conference of the IEEE', vol. 1, pp. 215-218.*

(Continued)

*Primary Examiner* — Patricia Mallari
*Assistant Examiner* — Jairo H Portillo
(74) *Attorney, Agent, or Firm* — Harness, Dickey & Pierce, PLC

(57) ABSTRACT

Methods are presented for determining pulse transit time (PTT) and/or pulse wave velocity (PWV) of a subject by application of parametric system identification to proximal and distal arterial waveforms. The two waveforms are measured from the subject. A system is defined that relates the proximal arterial waveform to the distal arterial waveform (or vice versa) in terms of the unknown parameters of a parametric mathematical model. The model parameters are determined from the measured waveforms using system identification. PTT between the proximal and distal arterial sites is then determined from the system model. PWV may (Continued)

also be determined by dividing the distance between measurement sites (D) by PTT.

24 Claims, 6 Drawing Sheets

(51) Int. Cl.
*A61B 5/029* (2006.01)
*A61B 5/00* (2006.01)

(56) References Cited

U.S. PATENT DOCUMENTS

| | | | | |
|---|---|---|---|---|
| 5,503,156 | A * | 4/1996 | Millar | A61B 5/021 600/485 |
| 5,558,096 | A * | 9/1996 | Palatnik | A61B 5/024 600/500 |
| 6,315,735 | B1 * | 11/2001 | Joeken | A61B 5/021 600/500 |
| 6,406,439 | B1 * | 6/2002 | Cohen | A61B 5/121 381/15 |
| 6,740,045 | B2 | 5/2004 | Amano | |
| 2002/0188205 | A1 * | 12/2002 | Mills | A61B 5/02028 600/481 |
| 2003/0036685 | A1 | 2/2003 | Goodman | |
| 2006/0149152 | A1 * | 7/2006 | Amitzur | A61B 5/02007 600/485 |
| 2006/0224073 | A1 * | 10/2006 | Lin | A61B 5/02007 600/513 |
| 2008/0221461 | A1 * | 9/2008 | Zhou | A61B 5/021 600/485 |
| 2009/0287097 | A1 | 11/2009 | Lowe | |
| 2010/0016736 | A1 | 1/2010 | Hahn et al. | |
| 2011/0263989 | A1 | 10/2011 | Mukkamala et al. | |
| 2011/0270098 | A1 | 11/2011 | Chowienczyk et al. | |

OTHER PUBLICATIONS

Fung et al, "Continuous Noninvasive Blood Pressure Measurement by Pulse Transit Time", 2004, 'Engineering in Medicine and Biology Society, 2004. IEMBS'04. 26th Annual International Conference of the IEEE', vol. 1, pp. 738-741.*

Francis, Said Elias. Continuous estimation of cardiac output and arterial resistance from arterial blood pressure using a third-order windkessel model. Diss. Massachusetts Institute of Technology, 2007.*

Pruett, J. D., J. D. Bourland, and L. A. Geddes. "Measurement of pulse-wave velocity using a beat-sampling technique." Annals of biomedical engineering 16.4 (1988): 341-347.*

Sugimachi, Masaru, et al. "A new model-based method of reconstructing central aortic pressure from peripheral arterial pressure." The Japanese journal of physiology 51.2 (2001): 217-222.*

Westerhof, Berend E., et al. "Individualization of transfer function in estimation of central aortic pressure from the peripheral pulse is not required in patients at rest." Journal of applied physiology 105.6 (2008): 1858-1863.*

McCombie et al, "Laguerre-Model Blind System Identification: Cardiovascular Dynamics Estimated From Multiple Peripheral Circulatory Signals", IEEE Transactions on Biomedical Engineering, vol. 52, No. 11, (Nov. 2005).

Redling, et al "Evaluation of the Tracking Potential of a Noninvasive Estimator of Cardiac Output", Comput. Biol. Med. vol. 26, No. 4, pp. 281-295 (1996).

Aakhus et al., "Non-invasive estimates of aortic root pressures: external subclavian arterial pulse tracing calibrated by oscillometrically determined brachial arterial pressures", Clinical Physiology, vol. 13, pp. 573-586 (1993).

Li et al., "Systolic time intervals in clinical pharamacology", European Journal of Pharamacology, vol. 44, pp. 415-421 (1993).

Hahn, Jin-Oh et al.: "A New Approach to Reconstruction of Central Aortic Blood Pressure Using "Adaptive" Transfer Function", Engineering in Medicine and Biology Society, 2008. EMBS 2008. 30th Annual International IEEE EMBS Conference, Piscataway, NJ, USA, Aug. 20, 2008 (Aug. 20, 2008), pp. 813-816, XP031508079.

Fetics, B et al.: "Parametric Model Derivation of Transfer Function for Noninvasive Estimation of Aortic Pressure by Radial Tonometry", IEEE Transactions on Biomedical Engineering, IEEE Service Center, Piscataway, NJ, USA, vol. 46, No. 6, Jun. 1, 1999, (Jun. 1, 1999), pp. 698-706, XP001035142.

Swamy, Gokul et al.: "Estimation of the Aortic Pressure Waveform from a Peripheral Artery Pressure Waveform via an Adaptive Transfer Function", Engineering in Medicine and Biology Society, 2008. EMBS 2008. 30th Annual International Conference of the IEEE, Piscataway, NJ, USA, Aug. 20, 2008 (Aug. 20, 2008), pp. 1385-1388, XP031508224.

Swamy, Gokul et al.: "Estimation of the Aortic Pressure Waveform from a Radial Artery Pressure Waveform via an Adaptive Transfer Function: Feasibility Demonstration in Swine", 2009 Annual International Conference of the IEEE Engineering in Medicine and Biology Society: EMBC 2009; Minneapolis, MN, USA, Sep. 3, 2009 (Sep. 3, 2009), pp. 2362-2364, XP031882626.

Swamy, Gokul et al.: "Quantification of Forward and Backward Arterial Waves by Model-Based Analysis of Aortic and Femoral Artery Pressure Waveforms", Engineering in Medicine and Biology Society, 2008. EMBS 2008. 30th Annual International Conference of the IEEE, Piscataway, NJ, USA, Aug. 20, 2008 (Aug. 20, 2008), pp. 817-820, XP031508080.

Hahn, Jin-Oh, et al.: "Sensitivity and Variance Analysis of Arterial Pressure Transfer Dynamics Estimated from Adaptive Multi-Channel System Identification", American Control Conference, 2007. ACC '07, IEEE, Piscataway, NJ, USA, Jul. 11-13, 2007, (Jul. 2007), pp. 613-618, XP031215213.

* cited by examiner

METHODS AND APPARATUS FOR DETERMINING ARTERIAL PULSE WAVE VELOCITY

CROSS-REFERENCE TO RELATED APPLICATIONS

This application is a 371 U.S. National Stage Application of International Application No. PCT/US2011/047516, filed on Aug. 12, 2011, which claims the benefit of U.S. Provisional Application No. 61/372,958, filed on Aug. 12, 2010. The entire disclosures of the above applications are incorporated herein by reference.

GOVERNMENT CLAUSE

This invention was made with government support under CBET0643477 awarded by the National Science Foundation. The government has certain rights in the invention.

FIELD

The present disclosure relates to more accurate methods for determining arterial pulse wave velocity of a subject.

BACKGROUND

Pulse wave velocity (PWV) is the speed of energy wave transmission in the arteries. According to the Bramwell-Hill equation, PWV varies inversely with the square root of arterial compliance (AC). Indeed, PWV increases as the arteries stiffen with aging and disease.

Due to the ease of its measurement, PWV has at least three potential clinical applications. First, PWV, as an index of arterial stiffness, has been shown to be an independent predictor of cardiovascular events and all-cause mortality in hypertensive and other patients. So, PWV may be used for risk stratification of, and guiding therapy in, these patients. Second, cardiac output (CO) determinations from blood pressure (BP) waveforms can only be obtained to within a scale factor that is often given by AC. Thus, PWV may be used to readily correct such determinations for AC changes and/or calibrate these determinations to absolute CO values. Third, since AC decreases with increasing BP, PWV and BP often show positive correlation. Hence, PWV may be used to realize continuous, non-invasive, and cuff-less BP monitoring.

Conventionally, PWV is measured as the ratio of the distance and pulse transit time (PTT) between proximal and distal arterial sites. PTT is, in turn, determined by acquiring waveforms from the two sites and then detecting the foot-to-foot time delay between the waveforms. The premise of this foot-to-foot detection method is that interference from the reflected wave is negligible during late diastole and early systole when the waveform feet occur. However, wave reflection interference may not always be trivial at the waveform feet. For example, at low heart rate (HR), the reflected wave adds constructively to the forward wave such that the method can grossly overestimate PWV. Just as important, the waveform feet are often difficult to detect, especially in the presence of waveform artifact. Thus, the foot-to-foot detection method is prone to error. Compounding matters, BP changes perturb PWV relatively little. As a result, even small PWV inaccuracies can lead to large errors in tracking BP. Indeed, typical plots of BP versus PWV show a great deal of scatter about the line of best fit. Such scatter obviously limits the ability of PWV to monitor BP.

Thus, there is a need for more accurate methods to determine PWV from two arterial waveforms. Such methods should be robust to artifact and avoid waveform misdetections while revealing the true PWV (i.e., the PWV in the absence of wave reflection). This section provides background information related to the present disclosure, which is not necessarily prior art.

SUMMARY

Methods are presented for determining PTT and/or PWV of a subject by application of parametric system identification to proximal and distal arterial waveforms. The two waveforms are measured simultaneously from the subject. A system is defined that relates the proximal arterial waveform to the distal arterial waveform (or vice versa) in terms of the unknown parameters of a mathematical model. The model parameters are determined from the measured waveforms using system identification. PTT between the proximal and distal arterial sites is then determined from the system model. PWV may also be determined by dividing the distance between measurement sites (D) by PTT.

In one aspect of the disclosure, the system that couples the two waveforms is defined as a parametric physical tube-load model transfer function, where one parameter explicitly represents the true PTT. All parameters of the transfer function are determined by coupling one waveform to the other and thus determining PTT as the true PTT parameter. PWV may then be determined as D/PTT.

In another aspect of this disclosure, the system that couples the proximal arterial waveform to the distal arterial waveform is defined by a parametric black-box model impulse response. The parameters of the impulse response are determined by coupling the proximal arterial waveform to the distal arterial waveform. PTT is determined as a time delay of the impulse response, and PWV may be determined as D/PTT.

This section provides a general summary of the disclosure and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

Figure 1:
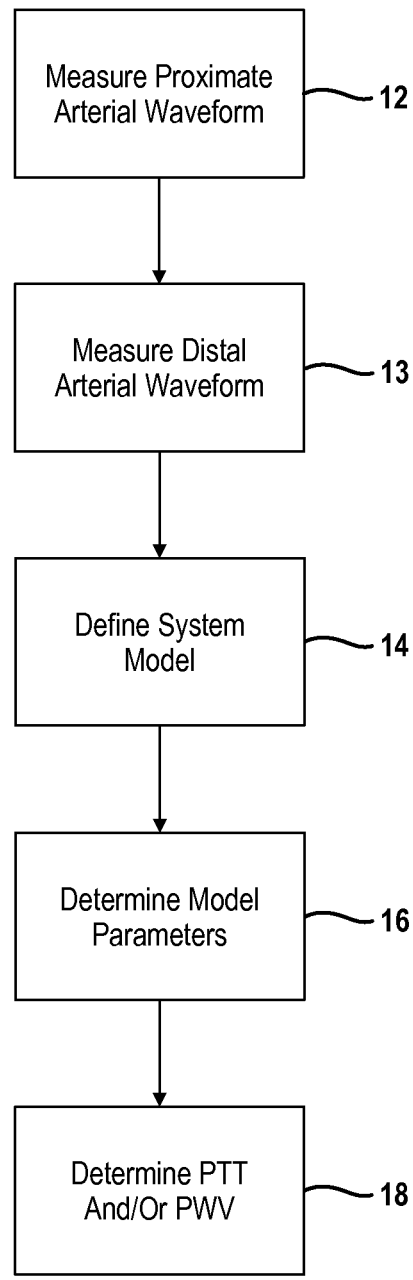
FIG. 1 is a flowchart depicting a general method for determining PWV of a subject.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 provides an overview of a method for determining PTT and/or PWV of a subject. A principal idea of this disclosure is to determine PTT and PWV of a subject by application of parametric system identification to proximal and distal arterial waveforms.

First, proximal and distal arterial waveforms are simultaneously measured at 12, 13. These waveforms are obtained at various sites such as the carotid and femoral arteries and represent BP, BV, blood flow rate, blood volume, or any other variable pertaining to the arterial pulse. The waveforms are measured using any of the methods known in the art. Exemplary methods include catheterization, electrocardiography (proximal only), tonometry, finger-cuff photoplethysmography (distal only), ultrasound, ballistocardiography (proximal only), electrical bioimpedance, pulse oximetry, laser Doppler vibrometry, infrared thermal imaging, and ultra wide band radar.

Second, a dynamic system relating one of the waveforms to the other waveform is defined through a parametric model at 14. In other words, the former waveform (typically the proximal arterial waveform) is regarded as the input to the system, whereas the latter waveform is considered to be the resulting output. The parametric model is based on physics such as a tube-load model of arterial wave transmission and reflection. Alternatively, the parametric model is not physically based such as the autoregressive exogenous input (ARX) model or any other member of the family of black-box models known in the art of system identification. (Note that black-box is used herein to refer to models expressed in terms of non-physical parameters.) The parametric black-box model may be linear (and thus characterized by a transfer function/impulse response) or nonlinear. The model parameters explicitly or implicitly represent the true PTT (i.e., the PTT in the absence of wave reflection). A key aspect here is the use of a parametric model. Unlike a nonparametric model, a parametric model assumes a specific structure in order to succinctly specify the system. Thus, the system may be more reliably identified from the limited information available in the two waveforms.

Third, the parameters of the system model are determined at 16 so as to couple or map the input to the output. Various techniques known in the art of system identification are used to determine the parameters such as regular, weighted, and total least squares parameter estimation as well as Laguerre basis functions.

Finally, PTT and PWV are determined at 18 from the system model. PTT is either determined as the model parameter that explicitly represents the true PTT or as the time delay of the system model using any of the tools known in the art of time delay estimation. Then, PWV is determined as D/PTT. Thus, PWV and PTT are effectively determined from the entire waveforms (rather than just their feet) after mathematically eliminating the reflected wave (by virtue of equalizing the waveform shapes) without involving waveform detections. In this way, the true PWV and true PTT may be accurately determined even in the presence of significant waveform artifact.

In one exemplary embodiment, central and peripheral BP or BV (or blood flow rate) waveforms are simultaneously measured. The system transfer function coupling the waveforms is defined in terms of the unknown parameters of a physical tube-load model of arterial wave transmission and reflection. The parameters explicitly represent the true PTT and other arterial properties. All parameters are determined by finding the transfer function, which when applied to one of the waveforms, best fits the other waveform. Finally, PWV is determined from PTT.

Figure 2A:
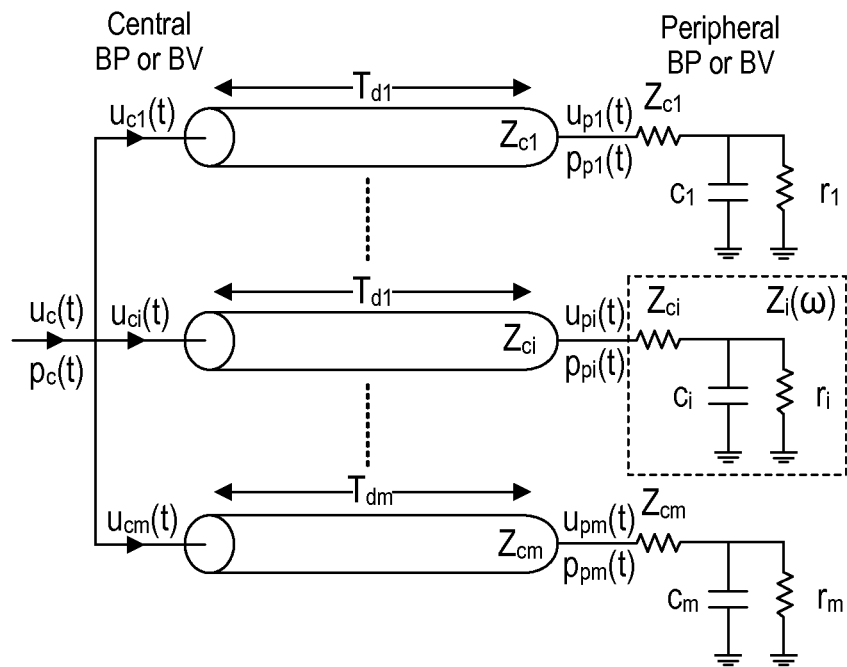
FIG. 2A is a diagram of an exemplary parametric tube-load model which may be used to represent wave transmission and reflection in the arterial tree of a subject.

More specifically, the arterial tree is modeled as m parallel, uniform tubes with terminal loads as shown in FIG. 2A. The $i^{th}$ tube represents the wave travel path between the central aorta and the $i^{th}$ peripheral artery. Each tube is frictionless and thus has constant characteristic impedance [$Z_{ci} = \sqrt{(\rho L_i/(A_i C_i))}$, where $L_i$, $A_i$, and $C_i$ are large artery length, area, and compliance] and allows waves to travel along the tube with constant PTT [$T_{di} = \sqrt{(\rho L_i C_i/A_i)}$]. The $i^{th}$ load represents the arterial bed distal to the $i^{th}$ peripheral artery. Each load has frequency-dependent impedance [$Z_i(\omega)$] characterized by peripheral resistance [$r_i$] and compliance [$c_i$] parameters while matching $Z_{ci}$ at high frequency. Waves traveling along a tube are reflected at the load according to the reflection coefficient [$(\Gamma_i(\omega) = (Z_i(\omega) - Z_{ci})/(Z_i(\omega) + Z_{ci})$] so as to predict the differences between actual BP and BV waveforms and the progressive changes that these waveforms undergo with increasing distance from the heart.

According to this model, the transfer functions relating a central BP or BV waveform [$p_c(t)$ or $u_c(t)$] to a peripheral BP or BV waveform [$p_{pi}(t)$ or $u_{pi}(t)$] may be defined in terms of $T_{di}$, $r_i c_i$, $Z_{ci} c_i$, and possibly $A_i Z_{ci}$ as set forth below.

central BP to peripheral BP transfer function:

$$p_c(t) \rightarrow \frac{jw + \frac{1}{r_i c_i} + \frac{1}{Z_{ci} c_i}}{\left(jw + \frac{1}{r_i c_i} + \frac{1}{2Z_{ci} c_i}\right) e^{jwT_{di}} + \frac{1}{2Z_{ci} c_i} e^{-jwT_{di}}} \rightarrow p_{pi}(t)$$

central BP to peripheral BV transfer function:

$$p_c(t) \rightarrow \frac{1}{A_i Z_{ci}} \frac{jw + \frac{1}{r_i c_i}}{\left(jw + \frac{1}{r_i c_i} + \frac{1}{2Z_{ci} c_i}\right) e^{jwT_{di}} + \frac{1}{2Z_{ci} c_i} e^{-jwT_{di}}} \rightarrow u_{pi}(t)$$

central BV to peripheral BP transfer function:

$$u_c(t) \rightarrow A_i Z_{ci} \frac{jw + \frac{1}{r_i c_i} + \frac{1}{Z_{ci} c_i}}{\left(jw + \frac{1}{r_i c_i} + \frac{1}{2Z_{ci} c_i}\right) e^{jwT_{di}} - \frac{1}{2Z_{ci} c_i} e^{-jwT_{di}}} \rightarrow p_{pi}(t)$$

central BV to peripheral BV transfer function:

$$u_c(t) \rightarrow \frac{jw + \frac{1}{r_i c_i}}{\left(jw + \frac{1}{r_i c_i} + \frac{1}{2Z_{ci} c_i}\right) e^{jwT_{di}} - \frac{1}{2Z_{ci} c_i} e^{-jwT_{di}}} \rightarrow u_{pi}(t)$$

Here, t and w denote time and frequency, respectively.

The three or four parameters are determined by finding the appropriate transfer function, which when applied to one of the waveforms, best fits the other waveform in the least squares sense. This fitting is performed in the time-domain by converting the transfer function into a recursive difference equation. The optimization is achieved through a numerical search over a physiologic range of the parameters. The parameters are determined for each beat or over multiple beats. The mean values of the waveforms are either removed prior to determining the parameters or kept intact. Lastly, PTT is determined as $T_{di}$, while PWV is determined as $D_i/T_{di}$, where $D_i$ is the distance between the two measurement sites. (When $A_i Z_{ci}$ is available, PWV may also be determined via the Waterhammer equation as described below. In this case, PWV may represent one or some combination of the two PWVs.)

At low HR (e.g., <60 bpm), the fitting can favor the upstroke and initial downstroke of the beat such that the $T_{di}$ unduly reflects these particular periods of the cardiac cycle. One way to obtain a $T_{di}$ representative of the whole beat is to divide the beat into two segments (e.g., of equal size), determine the parameters for each segment, and take an average of the two $T_{di}$. Another way is to weight the least squares fitting in favor of the latter part of the beat.

The above embodiment can be refined in several ways. For example, a tapered tube and/or a higher order or even optimal order terminal load may be employed to more accurately represent the arterial system. Other types of models and tools for determining the parameters are also contemplated within the broader aspects of this disclosure.

Figure 3A:
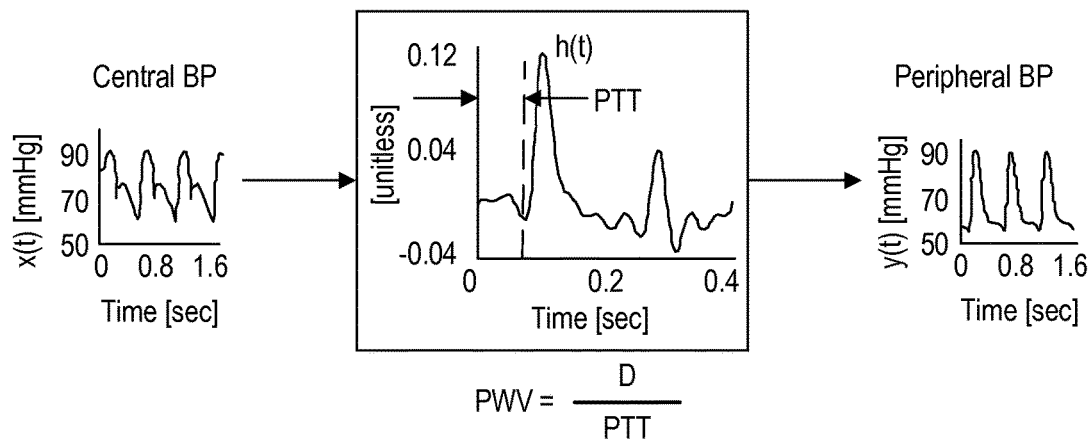
FIG. 3A is a diagram illustrating the estimation of PTT and PWV by identifying a parametric black-box model impulse response from any proximal arterial waveform and any distal arterial waveform.

In another exemplary embodiment, a system impulse response couples the waveforms as shown in FIG. 3A. In this embodiment, any proximal arterial waveform and any distal arterial waveform are simultaneously measured. The former waveform is regarded as the input (x(t)), while the latter waveform is considered to be the resulting output (y(t)). The system impulse response (h(t)) coupling the waveforms is defined in terms of the unknown parameters of a black-box ARX model. The parameters are determined by finding the h(t), which when convolved with x(t), best fits y(t). PTT is determined as the time delay of h(t), and PWV then is determined from PTT.

More specifically, the ARX model is given as follows:

$$y(t) = \sum_{k=1}^{n} a_k y(t-k) + \sum_{k=0}^{m} b_k x(t-k) + e(t),$$

where $\{a_k, b_k\}$ are unknown parameters, and n and m limit the number of parameters (model order), and e(t) is an unmeasured residual error. The term n is set to a constant value, while the term m should scale with PTT and is set to the PTT, as determined with the foot-to-foot detection method, scaled by the sampling rate. The parameters are then determined in closed-form from multiple beats of x(t) and y(t) by linear least squares minimization of e(t). The mean values of x(t) and y(t) are either removed prior to determining the parameters or kept intact. Since the time delay of h(t) is not an explicit parameter of the ARX model here, it is determined from h(t). In particular, the time delay is detected as the time of the maximal second derivative of h(t) between its first zero-crossing with positive derivative and its peak value. PTT is then determined as the time delay. This PTT may be viewed as the time delay between the entire x(t) and y(t) after equalizing their shapes. Lastly, PWV is determined as D/PTT.

At low HR, one way to obtain a PTT representative of the entire waveform is to divide each beat into two segments, determine the impulse response by fitting only the first segments of the multiple beats and by fitting only the second segments of these beats, and take an average of the time delays of the two impulse responses. Another way is to weight the least squares fitting in favor of the latter part of each beat.

The above embodiment can be refined in several ways. For example, a more complete black-box model such as the output error model may be employed. As another example, the model order may be adaptively determined from the waveforms via the MDL criterion or any other tool known in the art of system identification. As yet another example, the time delay of the impulse response may be determined using another feature such as the first zero crossover with positive derivative. Alternatively, PTT may be incorporated in the model explicitly through a time delay parameter. Other refinements are also contemplated within the broader aspects of this disclosure.

An ancillary aspect of this disclosure is to determine PWV of a subject by application of system identification to BP and BV waveforms from the identical sites. First, these waveforms are simultaneously measured at the same sites (or sites near each other) such as the carotid artery using any of the aforesaid methods. Then, the system coupling the BV waveform to the BP waveform (or vice versa) is defined through a parametric or nonparametric model. The model is physics-based or black-box and linear or nonlinear. The model represents the true arterial characteristic impedance (CI, i.e., the CI in the absence of wave reflection) scaled by the arterial area (A·CI) as an explicit parameter or implicitly. The system model is identified by coupling the waveforms. A·CI is then determined as the model parameter that explicitly represents the true A·CI or a feature of the system model. Finally, PWV is determined via the Waterhammer equation, A·CI/$\rho$, where $\rho$ is the blood density. Thus, PWV is again effectively determined from the entire waveforms after mathematically eliminating the reflected wave (by virtue of equalizing the waveform shapes). In this way, the true PWV may be accurately determined even in the presence of significant waveform artifact. By contrast, the conventional method for determining PWV via the Waterhammer equation is to find the slope of the line that relates just the early systolic samples of the waveforms, wherein wave reflection interference is assumed to be negligible.

In one exemplary embodiment, central BP and BV waveforms are simultaneously measured. The system transfer function coupling the waveforms is defined in terms of the unknown parameters of a physical tube-load model of arterial wave transmission and reflection. The parameters explicitly represent the true A·CI and other arterial properties. All parameters are determined by finding the transfer function, which when applied to one of the waveforms, best fits the other waveform. Finally, PWV is determined from A·CI.

Figure 2B:
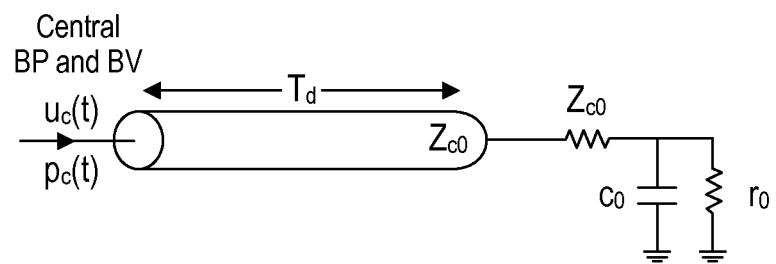
FIG. 2B is a diagram of another exemplary parametric tube-load model which may be used to represent wave transmission and reflection in the arterial tree of a subject.

More specifically, the arterial tree is modeled as a single uniform tube with terminal load as shown in FIG. 2B. The tube represents the wave travel path along a short segment of the aorta and likewise has constant CI [$Z_{c0}$] and allows waves to travel with constant PTT [$T_{d0}$]. The load represents the rest of the arterial tree and similarly has frequency-dependent impedance [$Z_0(\omega)$] characterized by the total peripheral resistance [$r_0$] and compliance [$c_0$] parameters while matching $Z_{c0}$ at high frequency.

According to this model, the transfer function relating the central BV waveform [$u_c(t)$] to the central BP waveform [$p_c(t)$] may be defined in terms of $T_{d0}$, $r_0c_0$, $Z_{c0}c_0$, and $A_0Z_{c0}$ as set forth below.

$$u_c(t) \to A_0Z_{c0}\frac{\left(jw + \frac{1}{r_0c_0} + \frac{1}{2Z_{c0}C_0}\right)e^{jwT_d} + \frac{1}{2Z_{c0}c_0}e^{-jwT_d}}{\left(jw + \frac{1}{r_0c_0} + \frac{1}{2Z_{c0}c_0}\right)e^{jwT_d} - \frac{1}{2Z_{c0}c_0}e^{-jwT_d}} \to p_c(t)$$

The parameters are determined from the waveforms as outlined above. Lastly, PWV is determined as $A_0Z_{c0}/\rho$, where $\rho$ is a nominal value for the blood density. This embodiment can likewise be refined in several ways.

Figure 3B:
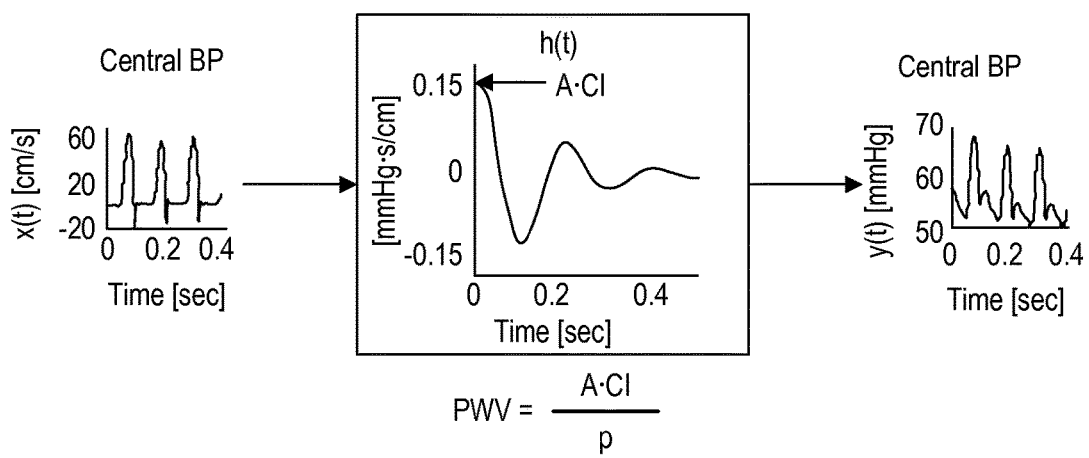
FIG. 3B is a diagram illustrating the estimation of PWV by identifying a parametric black-box model impulse response from BP and BV waveforms at the same site.
Figure 4A:
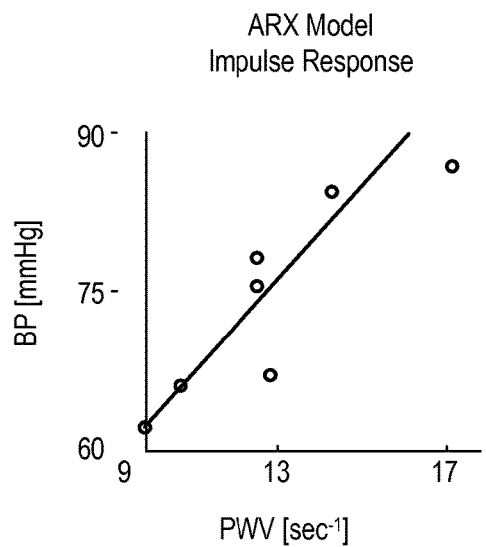
FIGS. 4A-4H are graphs illustrating results of some embodiments of this disclosure in terms of correlating positively with BP.
Figure 4B:
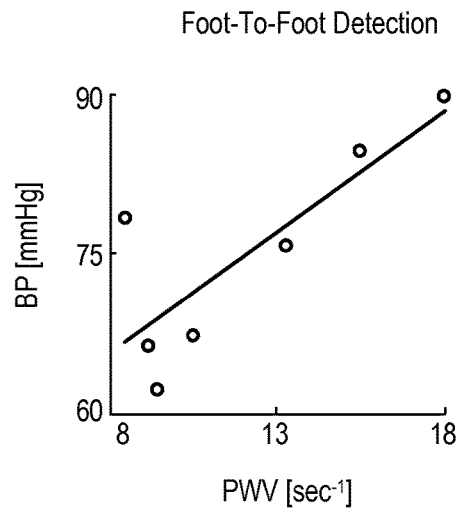
Figure 4C:
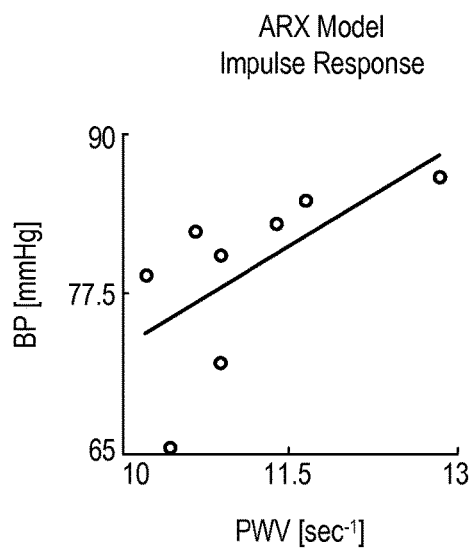
Figure 4D:
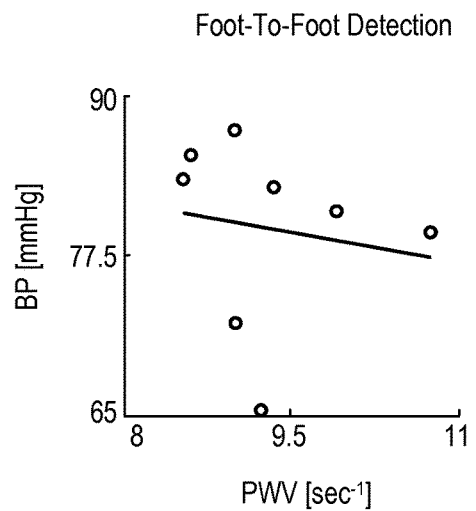
Figure 4E:
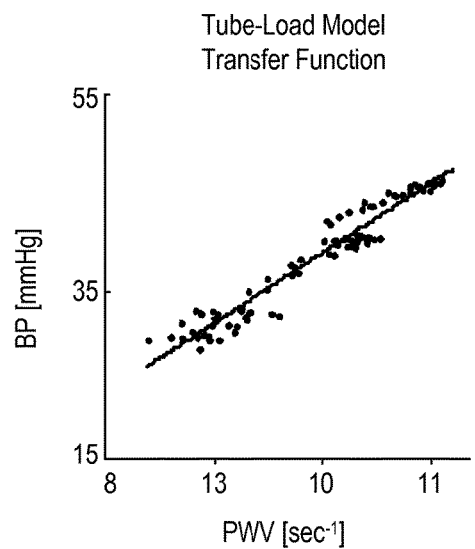
Figure 4F:
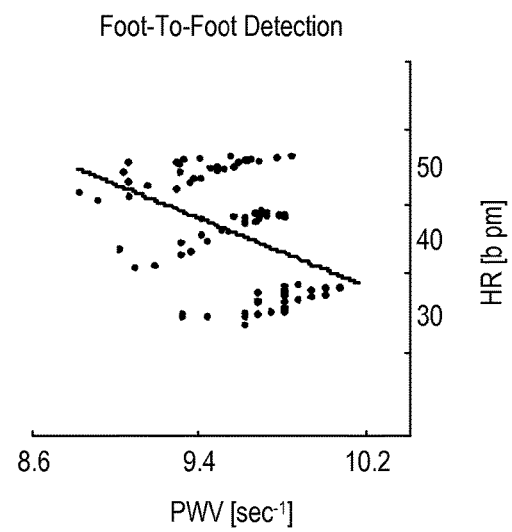
Figure 4G:
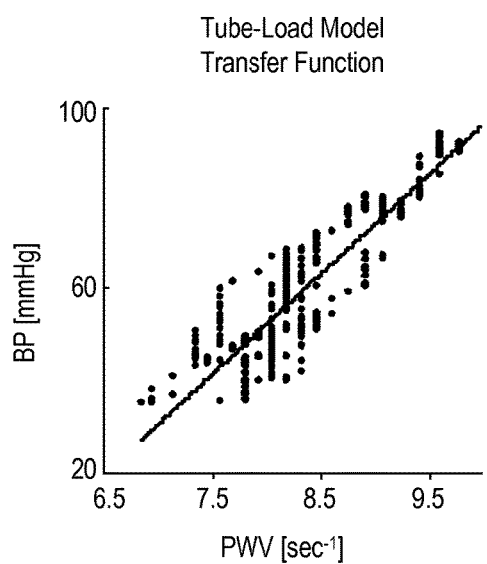
Figure 4H:
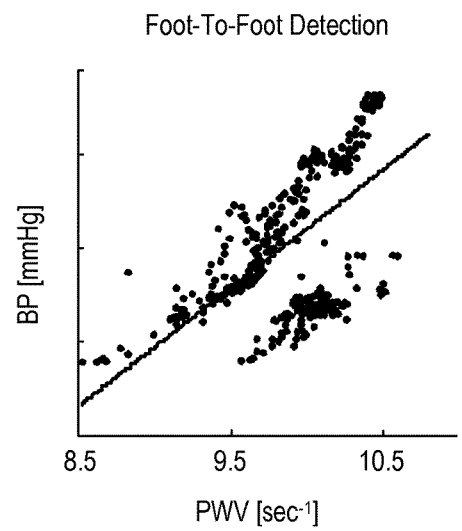

In another exemplary embodiment, a system impulse response couples the central BV waveform to the central BP waveform as shown in FIG. 3B. Central BV and BP waveforms are simultaneously measured. The former waveform is regarded as the input (x(t)), while the latter waveform is considered to be the resulting output (y(t)). The system impulse response (h(t)) coupling the waveforms is defined in terms of the unknown parameters of a black-box ARX model. The parameters are determined by finding the h(t), which when convolved with x(t), best fits y(t) as described above. A·CI is determined as the initial value of h(t) (i.e., h(0)) or the peak value of h(t). PWV is then determined as A·CI/$\rho$, where $\rho$ is again a nominal value for the blood density. This embodiment can also likewise be refined in several ways.

A third aspect of this disclosure is to determine PWV and PTT of a subject by application of system identification to two arterial waveforms that are sequentially (rather than simultaneously) measured as is sometimes done in practice. First, an ECG waveform is continuously acquired during the sequential measurements. Second, the impulse response relating an ECG-derived waveform to one of the arterial waveforms (at the same time period) is determined via a black-box model as described above. Third, the impulse response relating the same ECG-derived waveform to the other arterial waveform is likewise determined. Finally, one of the above embodiments is applied to the two impulse responses (rather than the two waveforms) to determine PWV and possibly PTT.

In an exemplary embodiment, central and peripheral BP waveforms are sequentially measured while an ECG waveform is simultaneously acquired. An impulse train is formed from the ECG waveform in which each impulse is located at an R-wave and has equal area. The impulse response coupling the impulse train to the central BP waveform at the same time period [$h_c(t)$] is determined via a black-box ARX model similar to what is described above. The impulse response coupling the impulse train to the peripheral BP waveform [$h_p(t)$] is then likewise determined. The parameters of the transfer function of the first equation herein are determined so as to map or fit $h_c(t)$ to $h_p(t)$ (or vice versa). All or some (e.g., initial portion) of the impulse response is fitted. At low HR, the impulse response is likewise divided into two segments or the fitting is weighted as described above. Finally, PTT is determined as $T_{di}$, and PWV is determined as D/PTT. This embodiment may be refined in several ways.

The above embodiments may be classified as either a physical model approach or a black-box model approach. Each approach holds advantages over the other. The black-box model approach for determining PWV from proximal and distal arterial waveforms is applicable to any waveform indicative of the arterial pulse rather than being limited to BP or BV waveforms. Further, the black-box model approach does not assume a specific model of arterial wave phenomena and should therefore be largely impervious to modeling error. On the other hand, by assuming a model, the physical model approach is able to extract PTT and A·CI not just from the time delay and scale factor of the transfer function but also from its shape and could consequently be more accurate. Moreover, this approach determines far fewer parameters due to the model assumption and can thus yield PTT over shorter time intervals (e.g., a beat) and be better suited to sequential measurements.

PWV and PTT determined as described above have several potential clinical applications. First, they may be used for more accurate arterial stiffness monitoring of hypertensive and other patients so as to direct their clinical management. For this application, PWV may be determined, for example, by identification of a tube-load model transfer function relating central and peripheral BP waveforms measured non-invasively via tonometry.

Second, the PWV and PTT may be used for accurate, continuous, non-invasive, and cuff-less BP monitoring. For this application, PTT may be determined, for example, by identification of an ARX model impulse response relating central and peripheral pulse oximetry waveforms. The peripheral waveform would preferably be measured from the lower body in order to arrive at PTT through the aorta in which confounding vasomotor tone is less of a factor. The PTT may then be mapped to BP using a previously constructed empirical calibration curve that relates PTT to BP for the subject. Indeed, some embodiments of the invention were tested in terms of the ability of their resulting PTT to correlate with BP in a subject during hemodynamic interventions. More specifically, PTT was determined by identification of (a) an ARX model impulse response relating a non-invasive impedance cardiography waveform (proximal arterial waveform) to a non-invasive peripheral BP waveform (distal arterial waveform) from humans during central blood volume reductions; (b) a tube-load model transfer function relating a high fidelity central BP waveform to a high fidelity peripheral BP waveform from an animal during low HR; and (c) a tube-load model transfer function relating a noisy central BV waveform to an invasive peripheral BP waveform from an animal during hemodynamic drug infusions. As revealed in FIG. 4, these embodiments showed significantly tighter correlation between BP and 1/PTT (i.e., proportional PWV) than the foot-to-foot detection method and even revealed positive correlation when the conventional method showed non-physiologic, negative correlation indicative of either significant waveform artifact or increasing overestimation of proportional PWV as HR decreased. These results are the first to demonstrate that system identification can indeed improve the determination of PTT and PWV from a pair of arterial waveforms.

Third, the PWV and PTT may be used to readily improve CO determinations from BP waveforms. More specifically, such determinations are often of the following form: CO/AC or CO·CI. If AC and CI were constant in a subject, then CO/AC and CO·CI would indicate the relative changes in CO in that subject and hence be useful for tracking a hemodynamic event or directing therapy. However, AC and CI are known to change with BP and vasomotor tone. These changes may become particularly problematic at the limits of the hemodynamic range. As indicated above, PTT=$\sqrt{(AL \cdot AC)}$, PWV=$D/\sqrt{(AL \cdot AC)}$, and CI=$\sqrt{(AL/AC)}$, where AL is the arterial inertance. So, the two forms are corrected for AC changes as follows: $PTT^2CO/AC$, $CO/(PWV^2AC)$, $PTT \cdot CO \cdot CI$, or $CO \cdot CI/PWV$. The new scale factor for the CO determinations is given by AL (and possibly D), which varies even less than AC in a subject. In this way, the accuracy of the CO determinations is enhanced. Any other CO determination from BP waveforms known in the art of pulse contour analysis can also be corrected for AC changes using PWV or PTT determined as described above.

In one exemplary embodiment, CO is determined from a BP waveform as PP·HR, where PP is the pulse pressure. PP is measured using any method known in the art such as systolic BP minus diastolic BP or the standard deviation of the BP waveform. Since this determination is of the CO/AC form, it is corrected for AC changes as follows: $PTT^2PP \cdot HR$ or $PP \cdot HR/PWV^2$.

In another exemplary embodiment, CO is determined from a BP waveform as described in U.S. Pat. No. 7,815,578 entitled, "Methods and Apparatus for Determining Cardiac Output" or U.S. Pat. No. 7,666,144 entitled, "Methods and Apparatus for Determining Cardiac Output and Left Atrial Pressure", both incorporated by reference herein. That is, first, the Windkessel time constant ($\tau$), which is equal to the product of the total peripheral resistance and AC, and possibly average venous pressure (VP) are determined. Then, CO is determined as $MAP/\tau$ or $(MAP-VP)/\tau$, where MAP is the mean BP. Since these determinations are also of the CO/AC form, they are corrected for AC changes as follows: $PTT^2MAP/\tau$, $MAP/(PWV^2\tau)$, $PTT^2(MAP-VP)/\tau$, or $(MAP-VP)/(PWV^2\tau)$. PTT and PWV here may alternatively be determined using any other method known in the art including the foot-to-foot detection method.

The CO determinations from BP waveforms may also be calibrated to absolute CO using the PWV and PTT as well as anthropomorphic information such as subject height, weight, and age. The basic idea is to first construct an empirical calibration curve that relates the scale factor, which is determined with the PTT or PWV, to anthropomorphic information using measurements obtained from a group of training subjects and to then determine the scale factor for a new testing subject by mapping her/his anthropomorphic information through the calibration curve. Any CO determination from BP waveforms known in the art of pulse contour analysis can be calibrated to absolute CO in this way.

In an exemplary embodiment, CO is determined as either $PTT^2PP \cdot HR$, $PTT^2MAP/\tau$, or $PTT^2(MAP-VP)/\tau$ as described above and is independently measured with an absolute method such as thermodilution or echocardiography from a group of subjects. Then, the ratios of the former CO determinations to the absolute CO measurements, which is equal to AL, are linearly or nonlinearly regressed against the ratios of the subject height and weight. Next, AL for a new subject is determined by mapping his height divided by weight through this calibration curve. Finally, $PTT^2PP \cdot HR/AL$, $PTT^2MAP/(\tau \cdot AL)$, or $PTT^2(MAP-VP)/(\tau \cdot AL)$ is determined for the subject to obtain an initial absolute CO in that subject. Subsequently, CO for the subject is likewise determined from his AL, an updated PP·HR, $MAP/\tau$, or $(MAP-VP)/\tau$, and either an updated PTT (so as to calibrate the CO determinations and correct them for AC changes) or the initial PTT (so as to only calibrate the CO determinations).

For these applications, PTT may be determined, for example, by identification of an ARX model impulse response relating central and peripheral arterial waveforms. The peripheral arterial waveform would preferably be measured from the lower body in order to arrive at PTT through the aorta, which mainly determines AC. Critically ill patients are routinely instrumented for continuous measurements of invasive radial BP, impedance pneumography, and pulse oximetry waveforms. So, in these patients, the impedance pneumography waveform (preferably with the heart bump maintained) and the pulse oximetry waveform as obtained from a toe may be conveniently used as the central and peripheral arterial waveforms, respectively. Alternatively, for even more convenient, but less efficacious, correction of AC changes, the radial BP waveform may be used as the peripheral arterial waveform. Finally, note that PP·HR, $MAP/\tau$, or $(MAP-VP)/\tau$ could be determined from the radial BP waveform as described above.

Figure 5:
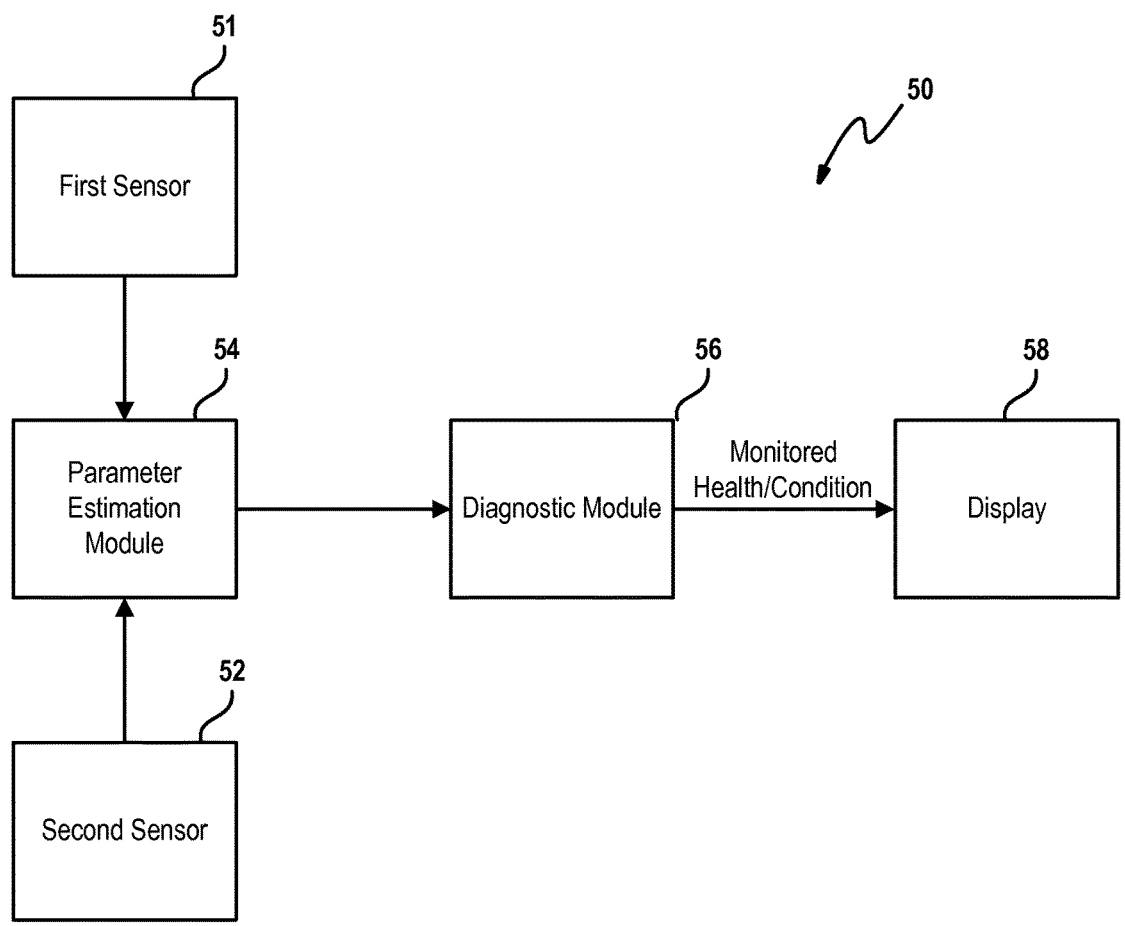
FIG. 5 is a diagram depicting an exemplary system for implementing the methods described in this disclosure.

Referring to FIG. 5, an exemplary system 50 is shown that implements one or more of the methods described above. The system 50 is comprised generally of two or more sensors 51, 52, a parameter determination module 54, a diagnostic module 56 and at least one output device 58 such as a display. However, it can be appreciated that the system 50 may include more or less sensors and modules. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality.

A first sensor 51 is configured to measure a waveform at a proximal arterial site of the subject, whereas the second sensor 52 is configured to measure a waveform at a distal arterial site of the subject. For example, the first and second sensors may be further defined as an applanation tonometer for measuring BP of the subject. In another example, the first and second sensors may be further defined as pulse oximeters. It is readily understood that other types of sensors fall within the scope of this disclosure.

The parameter determination module 54 determines the parameters of a system model that relates the proximal arterial waveform to the distal arterial waveform. To do so, the parameter determination module 54 receives the measured waveforms from the first and second sensors 51, 52 and samples the waveforms. The parameter determination module 54 then determines the parameters of the system model from the samples of the measured waveforms. The parameters are determined by implementing the various methods described above. In an exemplary embodiment, the model is pre-configured in a data store of the system and thus accessible to the parameter determination module 54.

Given the determined parameter values of the model, the diagnostic module 56 can compute either PTT or PWV of the subject. Each of these quantities has several clinical applications as described above such as tracking a subject's BP or improving CO determinations from BP waveforms. In some embodiments, the diagnostic module 56 may monitor computed quantities and trigger alarms when monitored quantities exceed thresholds. In other embodiments, the diagnostic module 56 may administer therapy to the subject or modify the subject's therapy, based on the monitored quantities. Lastly, the diagnostic module 56 may interface with the display 58 to present the monitored quantities on the display 58. However, it can be appreciated that other types of output devices may be used in lieu of the display device.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for determining an arterial pulse transit time of a subject, comprising:
   measuring a proximal waveform indicative of blood pressure at a proximal site of the subject using a first sensor;
   measuring a distal waveform indicative of blood pressure at a distal site of the subject using a second sensor;
   defining a dynamic system that relates one of the waveforms to the other waveform in terms of unknown parameters of a parametric mathematical model that assumes a specific structure for the dynamic system, where one of the unknown parameters accounts for wave reflection and another of the unknown parameters accounts for pulse transit time;
   determining the unknown parameters of the mathematical model from the measured proximal waveform and the measured distal waveform; and
   determining a pulse transit time between the proximal site and the distal site using the determined parameters from the mathematical model, where the steps of determining the unknown parameters of the mathematical model and determining a pulse transit time are implemented by a computer processor of a computing device.

2. The method of claim 1 further comprises determining a distance between the proximal and distal sites and determining a pulse wave velocity by dividing the distance by the pulse transit time.

3. The method of claim 1 further comprises determining the unknown parameters by fitting one of the proximal waveform or the distal waveform to the other waveform.

4. The method of claim 1 wherein the parametric mathematical model is a parametric physical tube-load model transfer function in which the pulse transit time is an explicit parameter of the model.

5. The method of claim 4 further comprises determining the parameters by finding the transfer function, which when applied to one of the waveforms, best fits the other waveform in a least squares sense.

6. The method of claim 1 wherein the mathematical model is a parametric black-box model that is characterized by non-physical parameters.

7. The method of claim 6 wherein the parametric black-box model is further defined as an impulse response.

8. The method of claim 7 further comprises determining the non-physical parameters by finding the impulse response, which when convolved with the proximal arterial waveform, best fits the distal arterial waveform in the least squares sense.

9. The method of claim 8 wherein the pulse transit time is determined as a time delay of the impulse response.

10. The method of claim 7 wherein the mathematical model is as an autoregressive exogenous input equation:

$$y(t) = \sum_{k=1}^{n} a_k y(t-k) + \sum_{k=0}^{m} b_k x(t-k) + e(t),$$

where y(t) is the distal waveform, x(t) is the proximal waveform, e(t) is an unobserved residual error, $\{a_k, b_k\}$ are unknown parameters that define the impulse response, and n and m represent the model order.

11. The method of claim 10 further comprises estimating the unknown parameters using a least squares method.

12. The method of claim 11 further comprises, for low heart rate, dividing a beat of the waveforms into two segments, determining the parameters of the transfer function for each of the two segments, and taking an average of the pulse transit time parameters for each of the two segments.

13. A method for determining an arterial pulse wave velocity of a subject, comprising:
   measuring a proximal waveform indicative of the arterial pulse at a proximal site of the subject using a first sensor;
   measuring a distal waveform indicative of the arterial pulse at a distal site of the subject using a second sensor;
   defining a dynamic system for the subject that relates one of the waveforms to the other waveform in terms of unknown parameters of a physical tube-load model transfer function in which pulse transit time is an explicit parameter of the model;
   determining the parameters of the transfer function from the measured proximal and the measured distal waveforms; and
   determining a pulse wave velocity from the pulse transit time parameter, where the steps of determining the parameters of the transfer function and determining a pulse transit velocity are implemented by a computer processor of a computing device.

14. The method of claim 13 wherein the waveforms are indicative of at least one of blood pressure, blood velocity, or blood flow rate.

15. The method of claim 13 further comprises measuring the proximal waveform from a carotid artery and measuring the distal waveform from a femoral artery.

16. The method of claim 13 wherein the physical tube-load model having a tube which is uniform and frictionless and represents a wave travel path between the proximal and distal arterial measurement sites, and a load distal to the distal measurement site, where the load has a frequency-dependence.

17. The method of claim 13 wherein the parameters are determined by finding the transfer function, which when applied to one of the waveforms, best fits the other waveform using a least square technique.

18. The method of claim 13 wherein determining pulse wave velocity further comprises determining a distance between the two measurement sites of the waveforms and determining the pulse wave velocity by dividing the distance by the pulse transit time parameter.

19. A method for tracking blood pressure of a subject, comprising:
  measuring a proximal waveform indicative of the arterial pulse at a proximal site of the subject using a first sensor;
  measuring a distal waveform indicative of the arterial pulse at a distal site of the subject using a second sensor;
  defining a dynamic system that relates the proximal arterial waveform to the distal arterial waveform in terms of a mathematical model, where one parameter of the mathematical model accounts for wave reflection and another parameter of the mathematical model accounts for pulse transit time;
  determining the mathematical model for the subject from the measured waveforms;
  determining a pulse transit time between the proximal site and the distal site from the mathematical model, where the steps of determining the mathematical model and determining a pulse transit time are implemented by a computer processor of a computing device; and
  tracking blood pressure by mapping the pulse transit time through a calibration curve that relates pulse transit time to blood pressure of the subject.

20. The method of claim 19 wherein the mathematical model is a parametric model that assumes a specific structure for the dynamic system.

21. A method for improving a cardiac output measure of a subject, comprising:
  measuring a waveform indicative of the arterial pulse at a proximal site of the subject using a first sensor;
  measuring a waveform indicative of the arterial pulse at a distal site of the subject using a second sensor;
  defining a dynamic system that relates the proximal arterial waveform to the distal arterial waveform in terms of a mathematical model, where one parameter of the mathematical model accounts for wave reflection and another parameter of the mathematical model accounts for pulse transit time;
  determining the mathematical model from the measured waveforms;
  determining a pulse transit time between the proximal site and the distal site from the mathematical model where the steps of determining the mathematical model and determining a pulse transit time are implemented by a computer processor of a computing device; and
  improving a cardiac output measure for the subject using the pulse transit time.

22. The method of claim 21 wherein the mathematical model is a parametric model that assumes a specific structure for the dynamic system.

23. The method of claim 21 further comprises improving a cardiac output measure from a blood pressure waveform by scaling it by an exponential of the pulse transit time so as to correct it for arterial compliance changes.

24. The method of claim 21 further comprises improving a cardiac output measure by calibrating it to absolute cardiac output using the pulse transit time and anthropomorphic information of the subject.

* * * * *